US00PP35073P2

(12) United States Plant Patent
Hansen

(10) Patent No.: US PP35,073 P2
(45) Date of Patent: Mar. 28, 2023

(54) ***DIANTHUS* PLANT NAMED 'LIP GLOSS'**

(50) Latin Name: ***Dianthus* hybrid**
Varietal Denomination: Lip Gloss

(71) Applicant: Hans A Hansen, Zeeland, MI (US)

(72) Inventor: Hans A Hansen, Zeeland, MI (US)

( * ) Notice: Subject to any disclaimer, the term of this patent is extended or adjusted under 35 U.S.C. 154(b) by 0 days.

(21) Appl. No.: 17/803,685

(22) Filed: Oct. 13, 2022

(51) Int. Cl.
*A01H 5/02* (2018.01)
*A01H 6/30* (2018.01)

(52) U.S. Cl.
USPC ..... Plt./281
CPC ..... *A01H 6/305* (2018.05)

(58) Field of Classification Search
USPC ..... Plt./281
CPC ..... A01H 6/305; A01H 5/02
See application file for complete search history.

*Primary Examiner* — Keith O. Robinson

(57) ABSTRACT

A new and unique plant cultivar of perennial carnation or pinks, *Dianthus* plant named 'Lip Gloss' with numerous, single, lightly-sweet fragrant flowers producing a full rounded face. Each flower has five overlapping petals that are rich magenta-pink-colored with white center eye and lighter pink edge. Petals have finely dentate apices and margins. Flowering season is strong for four weeks beginning in late spring and continues less densely to early-fall. The habit is compact and dense with glaucous blue-green foliage.

1 Drawing Sheet

Botanical denomination: *Dianthus* hybrid.
Cultivar designation: 'Lip Gloss'.

STATEMENT REGARDING PRIOR DISCLOSURES UNDER 37 CFR 1.77(B)(6)

The first enabling disclosure as a sale of the new plant was on Oct. 22, 2021 by Green Leaf Plants® (a division of Aris Horticulture, Inc.) which obtained the new plant from Walters Gardens, Inc. Walters Gardens, Inc. also introduced the new plant on Feb. 1, 2022, in the form of photographs and a brief description on a website operated by Walters Gardens, Inc. followed on Jun. 8, 2022, as a photograph and brief description in the "Walters Gardens 2022-2023 Catalog." Walters Gardens, Inc. obtained the plant and all information relating thereto, from the inventor. No plants of *Dianthus* 'Lip Gloss' have been sold, in this country or anywhere in the world, nor has any disclosure of the new plant been made more than one year prior to the filing date of this application, and such sale or disclosure within one year was either derived directly or indirectly from the inventor and would therefore be a 35 U.S.C. § 102b exception.

BACKGROUND OF THE INVENTION

The present invention relates to the new and distinct cultivar of carnation or pinks from the genus *Dianthus* and given the cultivar name 'Lip Gloss'. The new plant was the result of an intentional cross on Oct. 21, 2014, under the direction of the inventor between the proprietary, unreleased, unnamed hybrid known only by the breeder code 12-41-4 (not patented) as the female or seed parent and the male or pollen parent is the proprietary, unreleased, unnamed hybrid known only by the breeder code 12-60-1 (not patented). The cross was harvested and sown in the early spring of 2015. The new hybrid was first selected from trials at a wholesale perennial nursery in Zeeland, Mich.

during the summer of 2017 as a single seedling clone and given the breeder code number 14-11-1 later in the evaluation processes. *Dianthus* 'Lip Gloss' has been asexually propagated at the same nursery in Zeeland, Mich. since 2017 using traditional shoot tip cutting procedures and later sterile shoot-tip tissue culture and found to reproduce plants that are identical and exhibit all the characteristics of the original plant in successive generations.

SUMMARY OF THE INVENTION

*Dianthus* 'Lip Gloss' has not been evaluated under all possible environmental conditions. The phenotype may vary with variations in the environment including: growing temperature, available sunlight, nutrition, water, etc. without a change in the genotype of the plant.

The closest comparison plants to the new plant known to the inventor include: 'Paint the Town Magenta' U.S. Plant Pat. No. 29,222, 'Paint the Town Fuchsia' U.S. Plant Pat. No. 28,636, KAHORI® 'Pink' (not patented), 'Fuchsia Fire' (not patented), 'Neon Star' U.S. Plant Pat. No. 14,549, and 'Wp11 Tyr04' U.S. Plant Pat. No. 25,077.

'Paint the Town Magenta' has a slightly smaller habit and foliage and the flowers are slightly smaller and of vibrant magenta-pink, and does not have the white eye. 'Paint the Town Fuchsia' has similar slightly smaller habit and foliage, and the flowers are smaller and have lavender centers. KAHORI® 'Pink' has less vigorous habit, the flower petals are less overlapping and have a more deeply dentate apical margin. 'Fuchsia Fire' has similar habit and foliage, and the flowers are darker fuchsia-colored, with a solid fuchsia eye, and with more deeply dentate apical margin. 'Neon Star' has a smaller habit in side-by-side growing trials at the same age, and flowers that are darker red with an identical dark-red colored center without a white eye. 'Wp11 Tyr04' has a flower with a more concentrated reddish eye that radiates toward the margin.

The female parent, 12-41-4, has a semi-double flower with wider petals. The male parent, 12-60-1, had a taller habit and the flowers are smaller and the dark red eye was more significant.

*Dianthus* 'Lip Gloss' is distinct from its parents and all other *Dianthus* known to the applicant in the following combined traits:

1. Single flowers with five overlapping petals forming a full rounded face;
2. Petals have finely dentate apices;
3. Petal color is a rich magenta-pink with a white center eye and lighter pink edge;
4. Numerous flowers per plant on heavily branched upright sterns;
5. Prolonged flowering period with a strong flush in late spring and continuing to early-fall;
6. Compact habit and dense, glaucous, blue-green foliage.

BRIEF DESCRIPTION OF THE DRAWINGS

The photographs of 'Lip Gloss' are of a two-year-old plant grown in full-sun trial garden in Zeeland, Mich. showing the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
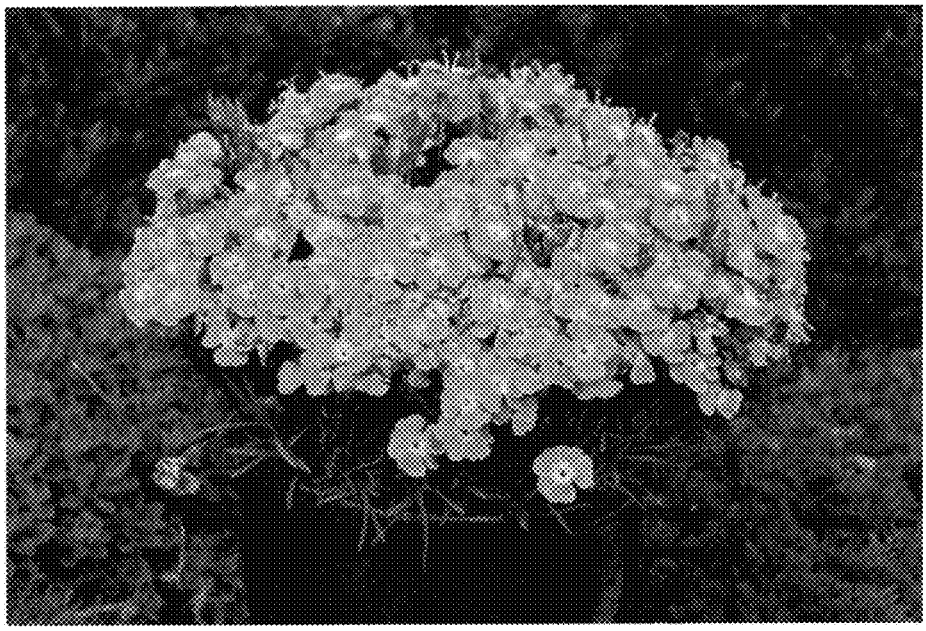
FIG. 1 shows the habit of the plant in mid-season flowering.
Figure 2:
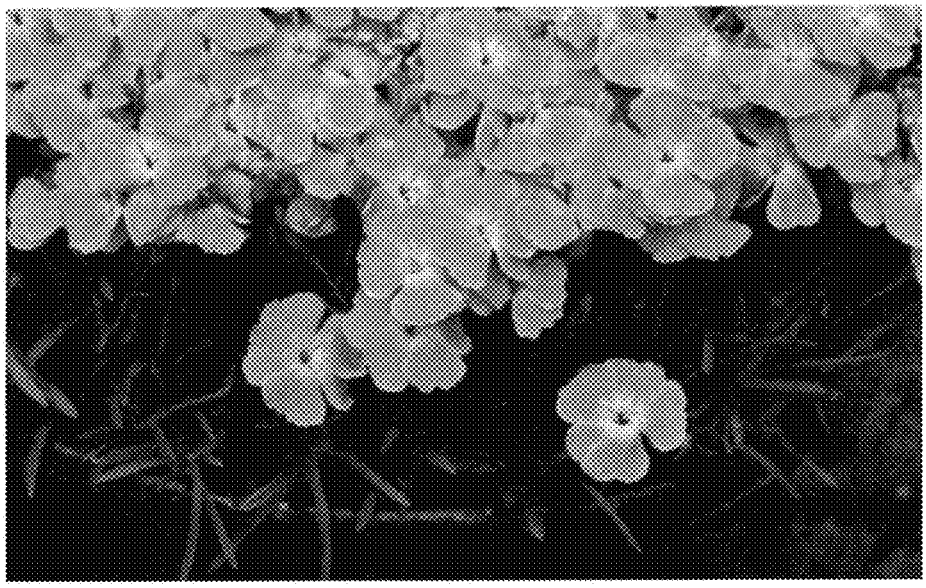
FIG. 2 shows a close-up of the flowers and buds.

The following detailed description of 'Lip Gloss' is based on observations of two-year-old plants in a full-sun trial garden at a nursery in Zeeland, Mich. with supplemental watering, light additions of fertilizer and free of other plant growth regulators. All color usage is in accordance with the 2015 edition of The Royal Horticultural Colour Chart except where common dictionary terms are used.

Botanical classification: *Dianthus* hybrid;

Parentage: The female or seed parent is 12-41-4; the male or pollen parent is 12-60-1;

Plant habit: Caespitose, herbaceous, evergreen, winter-hardy perennial; stems and peduncles highly branched, mostly erect stems to slightly arching; height of foliage about 13.5 cm and about 28 cm across; height in flower is about 16 cm;

*Root system*.—Fine, fibrous; color nearest RHS 155D depending on soil substrate and nutrition.

*Vigor*.—Very good, spring planted plugs finish in 3.8-liter pots in six to eight weeks.

Foliage:

*Leaf type*.—Simple, linear, opposite, decussate, sessile, glabrous, glaucous both adaxial and abaxial; margin entire; apex narrowly acute; base truncate, decurrent, clasping; straight; no fragrance detected; glaucosity medium.

*Leaf dimensions*.—To about 60 mm long and about 4 mm wide near middle, average about 48 cm long and 3 mm wide.

*Leaf color*.—Young expanding adaxial base nearest RHS 145C and distally nearest RHS 138B, abaxial base nearest RHS 145C and distally nearest RHS 138B; mature adaxial base nearest RHS 145C and distally between RHS N138A and RHS 189A, abaxial base nearest RHS 145C and distally between RHS N138A and RHS 189A.

*Venation*.—Not pronounced; obscurely pinnate, coloration same as that of adaxial and abaxial.

Stems: About 100 per plant; upright; cylindrical, hollow; glabrous; glaucous; branching in upper nodes;

*Stem size*.—About 13 cm long to peduncle and about 2.5 mm wide at base.

*Stem color*.—Variable depending on light exposure, with little to no light exposure nearest RHS 149D, with moderate to high light exposure between RHS N138A and RHS 189A.

*Branching*.—Numerous; typically alternate from lower nodes; about 12 per main stem and about 200 per plant in late spring peak; branch size average about 5.5 cm long and 1.0 mm diameter at time of initial flowering.

*Nodes*.—About 4.0 mm across; color nearest RHS N189A in high light and nearest RHS 149D in low light.

*Internodes*.—About 10 to 12 per stem before peduncle; average about 5 mm apart depending on growing temperature, shorter in cooler conditions.

*Inflorescence*.—Flowering in the upper 4.0 cm and to about 6.5 cm across; with an average of two flowers per inflorescence.

*Flower bud*.—With calyx still closed and petals style contain within calyx: slowly opening; glabrous; glaucous; cylindrical with attenuate base and acute apex; about 28 mm long and 5 mm across.

*Flower bud color*.—Nearest RHS 137A.

Flower:

*Type*.—Terminal, cymose; perfect; salverform; actinomorphic; single.

*Attitude*.—Upright to slightly outwardly around perimeter of plant.

*Dimension*.—About 3.5 cm across and extending about 3.3 cm above base of calyx tube, calyx tube to about 25 mm tall and 5 mm wide at apex of calyx.

*Flowers per stem*.—Up to 3, average 2.

*Pedicel*.—Glaucous, glabrous, cylindrical, stiff; primarily upright.

*Pedicel size*.—To about 33 mm long and about 1.5 mm diameter.

*Pedicel color*.—Between N138A and RHS N189C.

*Flower period*.—Beginning in late May with a strong flush for about four weeks and continuing more sparsely through mid-fall.

*Flower fragrance*.—Lightly sweet, spicy.

*Flower lasting quality*.—Individually about seven to ten days on or cut from plant.

*Corolla profile*.—Flat.

*Petals*.—Five; glabrous adaxial and abaxial except at proximal half of adaxial limb puberulent; consisting of a limb and a claw; limb obdeltoid, and limb and claw combined are flabellate; limb apex and margin finely dentate to crenate, with teeth to about 1 mm long and 1 mm wide at base; limb base attenuate toward claw; claw with attenuate base; bent outwardly at limb base creating a flat rounded face; persistent; having a lighter eye.

*Petal dimensions*.—Limb to about 16 mm long and 18 mm wide; claw about 21 mm long and 6 mm wide tapering to attenuate base of about 1 mm across; whole petal to about 37 mm long, average about 36 mm long; lighter eye about 10 mm across, and thin 0.5 mm wide lighter distal adaxial margin.

*Petal color*.—Young adaxial limb distal margin nearest 68B, middle between RHS N74A and RHS 64A, center eye before claw nearest 69C with darker veins of nearest RHS 64A extending into the limb about 5 mm, claw nearest RHS 145C proximally with distal claw before limb nearest RHS NN155C; young abaxial limb nearest RHS 71C and transitioning to nearest RHS NN74D toward margin, claw nearest RHS 145C proximally with distal claw before limb nearest RHS NN155C; mature adaxial limb between RHS N74A and RHS 67B with margin variable between RHS 68B and RHS 65B, center eye before claw nearest 69C with darker veins of nearest RHS 64A extending into the limb about 5 mm, claw base nearest RHS 145D with middle nearest RHS 145C and distally nearest RHS NN155C; mature abaxial limb young and mature adaxial limb nearest RHS N74D around margin, nearest RHS 69C in center eye and between RHS 71D and RHS NN74D in the middle, claw base nearest RHS 145D, middle nearest RHS 145C and before limb nearest NN155C.

*Calyx*.—Tubular; to about 22 mm long and 5 mm diameter at apex.

*Sepals*.—Five; acute apex and fused in basal 17 mm forming five-toothed calyx tube; glabrous adaxial and abaxial; glaucous abaxial; margins entire.

*Sepal size*.—Individually about 22 mm long and about 3.5 mm across at fusion.

*Sepal color*.—Adaxial nearest RHS 137A; abaxial nearest RHS 146D without significant anthocyanin observed.

*Peduncle*.—Glabrous; glaucous; hollow, cylindrical; stiff; about 3 cm long and about 2 mm diameter at base; attitude mostly upright to slightly arching.

*Peduncle color*.—Blend nearest RHS N138B and RHS 189C with light glaucous bloom.

*Epicalyx*.—Two pairs subtending each flower; both pairs adpressed; opposite; lightly glaucous, glabrous; sessile, margin entire; ovate to obtuse; inner pair narrowly acute apex and truncate base, 9 mm long and about 4 mm across near middle; outer pair with very short narrowly acute apex, truncate clasping base, about 10 mm long and about 3 mm wide.

*Epicalyx color*.—Both pairs adaxial and abaxial margin nearest RHS 145C and center to apex nearest RHS 137A; no anthocyanin pigment observed.

*Androecium*.—Typically 12 in two sets of 6 dehiscing in sequence about 3 days apart. Filaments: initially straight, curving outwardly with maturity; to about 27 mm long and 0.5 mm diameter; color nearest RHS NN155B, distally developing slight blush nearest RHS 72B; Anther: oblong; basifixed; about 2.5 mm long and 1.5 mm across; color nearest RHS 76C; Pollen: abundant; color nearest RHS 96D.

*Gynoecium*.—Single; to about 27 mm long. Style: bifurcate just above ovary; shoulder absent; puberulent adaxial one-third; to 17 mm long and 1.0 mm diameter; color proximally nearest RHS NN155C, distally between RHS 76C and RHS 72B, hairs proximally nearest RHS 71A; Stigma: globose; puberulent along distal surface; about 0.5 mm long and 0.5 mm wide; color nearest RHS 72B; Ovary: superior; cylindrical; acute apex and truncate base; smooth, lustrous; about 7 mm long and 3 mm diameter; color distally nearest RHS 145A and proximally nearest RHS 150D.

Fruit: Not observed;

Disease resistance: The new plant is resistance to center die out from fungus or high temperatures.

Growth: The plant grows best with adequate moisture and well-drained soil but tolerates some drought once established. Hardiness at least from USDA zone 4 through zone 9.

It is claimed:

1. A new and distinct *Dianthus* plant named 'Lip Gloss' essentially as herein described and illustrated.

* * * * *